US012661042B2

(12) United States Patent
Kanzaki

(10) Patent No.: US 12,661,042 B2
(45) Date of Patent: Jun. 23, 2026

(54) MEASUREMENT DEVICE

(71) Applicant: ARKRAY, Inc., Kyoto (JP)

(72) Inventor: Yuto Kanzaki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 421 days.

(21) Appl. No.: 18/470,894

(22) Filed: Sep. 20, 2023

(65) Prior Publication Data

US 2024/0138733 A1     May 2, 2024

(30) Foreign Application Priority Data

Oct. 26, 2022     (JP) ................................. 2022-171799

(51) Int. Cl.
*A61B 5/15*          (2006.01)

(52) U.S. Cl.
CPC .............................. *A61B 5/150633* (2013.01);
*A61B 2562/0295* (2013.01)

(58) Field of Classification Search
CPC ...... A61B 5/150633; A61B 2562/0295; B01L
3/5023; B01L 2200/025; B01L 2300/046;
B01L 2300/0825; B01L 2400/0406;
G01N 27/3273; G01N 33/4875
See application file for complete search history.

(56) References Cited

U.S. PATENT DOCUMENTS 5,526,120 A   *   6/1996   Jina .................... G01N 21/8483
                                                                356/423
7,846,387 B2 *  12/2010  Arbogast ........... G01N 33/4875
                                                                422/537

8,475,732 B2 *   7/2013   Simmons ........... A61B 5/14532
                                                                600/347
2008/0166269 A1   7/2008   Jansen
2012/0252133 A1  10/2012   Faulkner et al.
2020/0122151 A1 *  4/2020   Schramm ............ A61M 5/1723
2022/0299501 A1   9/2022   Julien et al.

FOREIGN PATENT DOCUMENTS

JP          2011-232170 A     11/2011

OTHER PUBLICATIONS

The extended European search report issued by the European Patent Office on Feb. 23, 2024, which corresponds to European Patent Application No. 23204377.8-1001 and is related to U.S. Appl. No. 18/470,894.

* cited by examiner

*Primary Examiner* — Jason M Sims
*Assistant Examiner* — Ari S Padda
(74) *Attorney, Agent, or Firm* — Studebaker Brackett PLLC

(57)          ABSTRACT

A protective cover is attached to a measurement device. The measurement device is provided with an insertion aperture for insertion of a test strip onto which a liquid sample is spotted. The protective cover is attached to the measurement device so as to cover a region including surroundings of the insertion aperture. The protective cover is provided with an opening portion into which the test strip is insertable. The opening portion and the insertion aperture are relatively positioned such that, in a state in which the test strip is inserted through the opening portion and inserted into the insertion aperture, an upper face and lower face of the test strip both abut against the protective cover.

9 Claims, 11 Drawing Sheets

FIG.10

MEASUREMENT DEVICE

CROSS-REFERENCE TO RELATED APPLICATION

This application claims priority under 35 USC 119 from Japanese Patent Application No. 2022-171799, filed on Oct. 26, 2022, the disclosure of which is incorporated by reference herein.

BACKGROUND

Technical Field

The present invention relates to a measurement device for measuring a sample in a liquid state, and particularly to a blood sugar measurement device.

Related Art

Heretofore, various measurement devices have been provided in which a disposable test strip is inserted into an insertion aperture of a blood sugar measurement device, a blood sample is spotted onto the test strip, and a blood sugar value of the blood sample is measured. In this type of measurement device, when a blood sample of an amount exceeding a proper amount is spotted onto the test strip, the surplus blood sample passes along the test strip and ingresses into the measurement device, which leads to soiling and malfunction of the measurement device.

In an attempt to solve this problem, the technology described in Japanese Patent Application Laid-Open (JP-A) No. 2011-232170 has been disclosed. In this technology, to prevent blood from ingressing to the interior of a device, a pair of doors are provided that allow insertion of a test strip into the device. The pair of doors abut against the test strip, as a result of which the opening of the device is closed up to be liquid-tight.

According to the technology described in JP-A No. 2011-232170, to prevent the ingression of blood, the device as a whole must increase in size and become more complicated in structure, leading to an increase in cost of the device as a whole. An embodiment of the present disclosure provides a measurement device that can, with a simple structure, prevent a surplus blood sample spotted onto a test strip from ingressing into the measurement device through an insertion aperture of the measurement device, and thus can prevent soiling and malfunction.

SUMMARY

An embodiment of the present disclosure is a measurement device to which a protective cover is attached. The measurement device is provided with an insertion aperture for insertion of a test strip onto which a liquid sample is spotted. The protective cover is attached to the measurement device so as to cover a region including surroundings of the insertion aperture, and the protective cover is provided with an opening portion into which the test strip is insertable. The opening portion and the insertion aperture are relatively positioned such that, in a state in which the test strip is inserted through the opening portion and inserted into the insertion aperture, an upper face and a lower face of the test strip both abut against the protective cover.

According to the embodiment of the present disclosure, a measurement device is provided that can prevent a surplus blood sample spotted onto a test strip from ingressing into the measurement device through an insertion aperture of the measurement device, and thus can prevent soiling and malfunction.

BRIEF DESCRIPTION OF THE DRAWINGS

Exemplary embodiments will be described in detail based on the following figures, wherein:

FIG. 10 schematically shows flows of a surplus blood sample at a rear face side of the protective cover.

DETAILED DESCRIPTION

Figure 1:
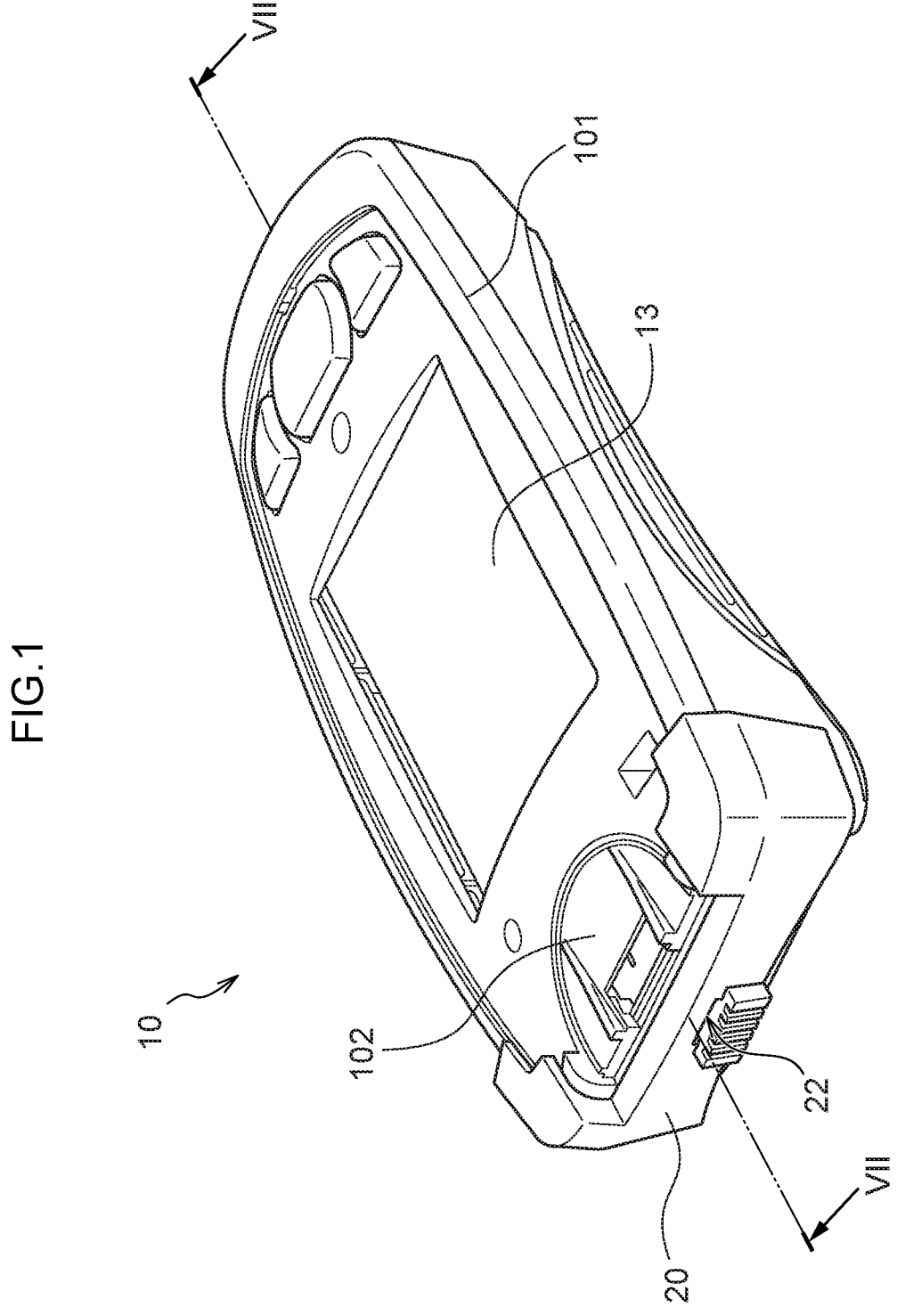
FIG. 1 is a front-upper perspective view of a measurement device according to an exemplary embodiment.

An exemplary embodiment of the present disclosure is described below with reference to the drawings. Reference symbols that appear in multiple drawings indicate the same parts unless particularly specified. Members and portions illustrated in the drawings are merely schematic depictions and do not necessarily accurately represent sizes and relative positions of actual components, and shapes and locations of detailed portions in the drawings are not always consistent. The present disclosure relates to a measurement device for measuring a liquid sample but, for convenience of description, a blood sugar measurement device that measures a blood sample serving as the liquid sample is described as an example of the measurement device.

Figure 2:
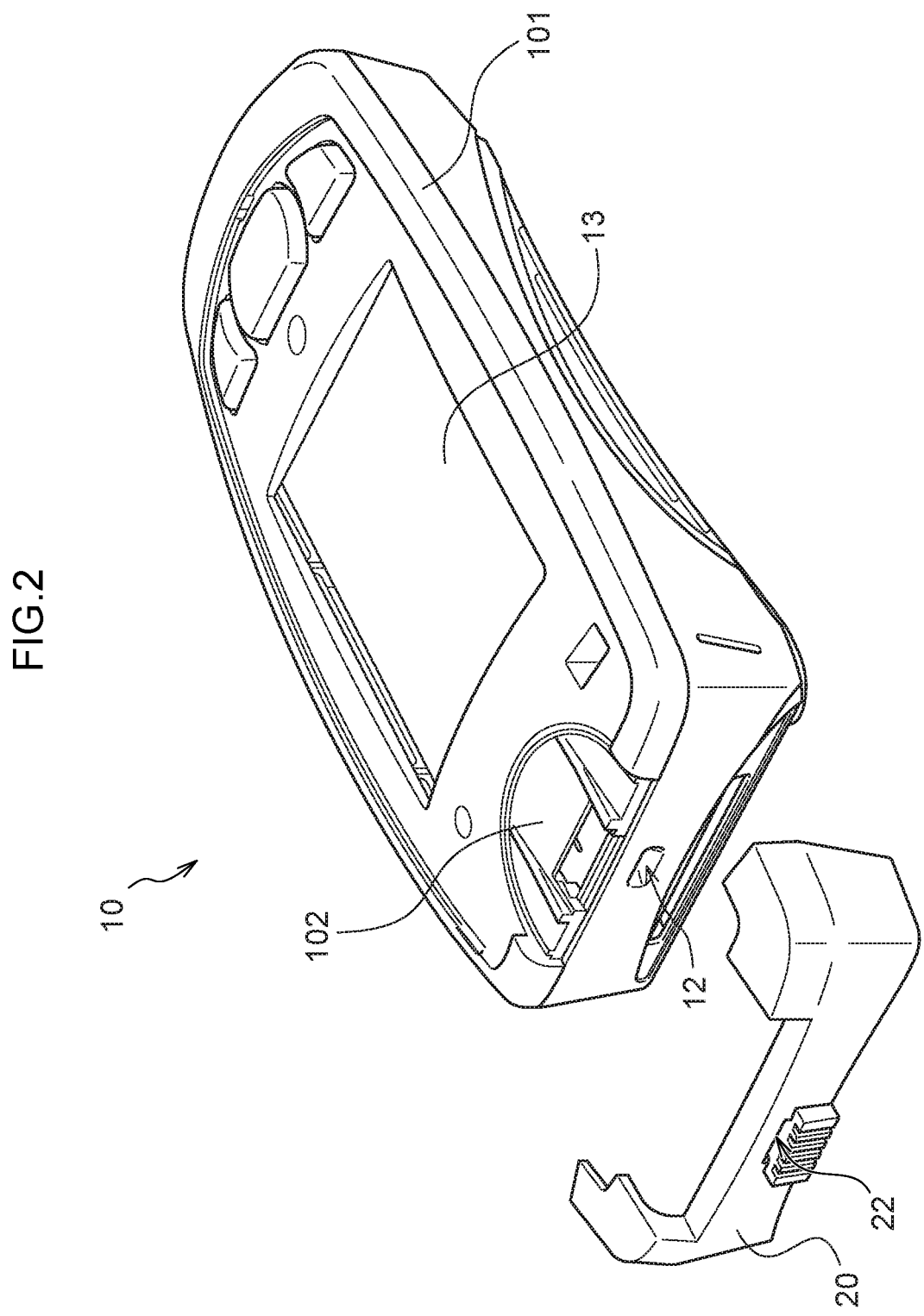
FIG. 2 is a front-upper perspective view of the measurement device in FIG. 1, showing a state in which a protective cover is removed.

Overall structure of a measurement device 10 is described with reference to FIG. 1 and FIG. 2. FIG. 1 is a front-upper perspective view of the measurement device 10 according to an exemplary embodiment of the present disclosure. Moreover, FIG. 2 is a front-upper perspective view showing the measurement device 10 of FIG. 1 in a state in which a protective cover 20 is removed. The measurement device 10 is structured with a substantially box-shaped casing body 101 and a measuring instrument 102 (see FIG. 7). Four corners of the casing body 101 are formed in curved shapes. The measuring instrument 102 measures a test strip 50 which is described below (see FIG. 8). That is, the casing body 101 is a protective member enclosing the measuring instrument 102, and the casing body 101 forms the exterior of the measurement device 10. A display unit 13 is formed at a top face of the casing body 101. A user views measurement results of the measuring instrument 102 via the display unit 13. A bottom face of the casing body 101, which is at the opposite side thereof from the top face at which the display unit 13 is provided, is not shown in the drawings.

In FIG. 1, the protective cover 20, which is a separate body, is attached to an end portion of the measurement device 10 at which the test strip 50 is to be inserted. In the present disclosure, in a state in which the display unit 13 faces upward, the side at which the protective cover 20 is provided is referred to as a "front face" or a "forward face", and the opposite side of the measurement device 10 is referred to as a "rear face". A direction connecting the front face (forward face) and rear face is referred to as a "front-rear direction". A direction toward the display unit 13 is referred to as "upward" and the opposite direction is referred to as "downward". A direction connecting upward and downward is referred to as a "vertical direction". In accordance with these positional relationships, a direction that is orthogonal to the front-rear direction and the vertical direction is referred to as a "left-right direction".

As shown in FIG. 2, an insertion aperture 12 is provided in a central portion of the front face side of the measurement device 10. The insertion aperture 12 is for insertion of the test strip 50, onto which a liquid sample is spotted. The insertion aperture 12 is formed in a front face end portion of the measurement device 10 as a slit that extends in the left-right direction. On the other hand, an opening portion 22 into which the test strip 50 can be inserted is provided at a central portion of the protective cover 20. The opening portion 22 is formed in the central portion of the protective cover 20 as a slit that extends in the left-right direction. The opening portion 22 penetrates between the front and rear of the protective cover 20. The protective cover 20 is attached to an end portion at the front face side of the measurement device 10 so as to cover a region that includes surroundings of the insertion aperture 12 in the front face side of the measurement device 10. Relative positions of the opening portion 22 and the insertion aperture 12 in the state in which the protective cover 20 is attached to the measurement device 10 are described in more detail below.

Figure 3:
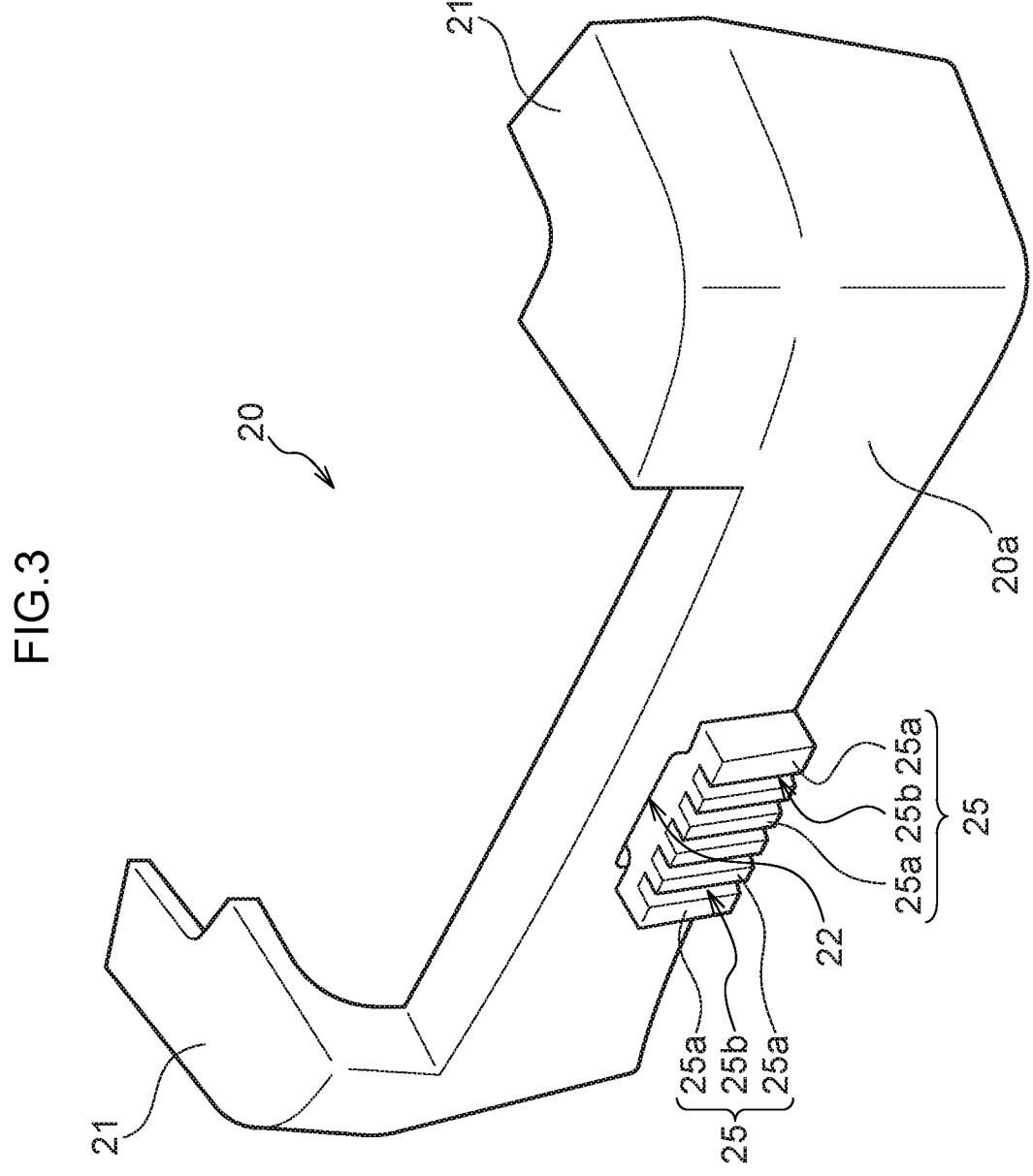
FIG. 3 is a front-upper perspective view of the protective cover.
Figure 4:
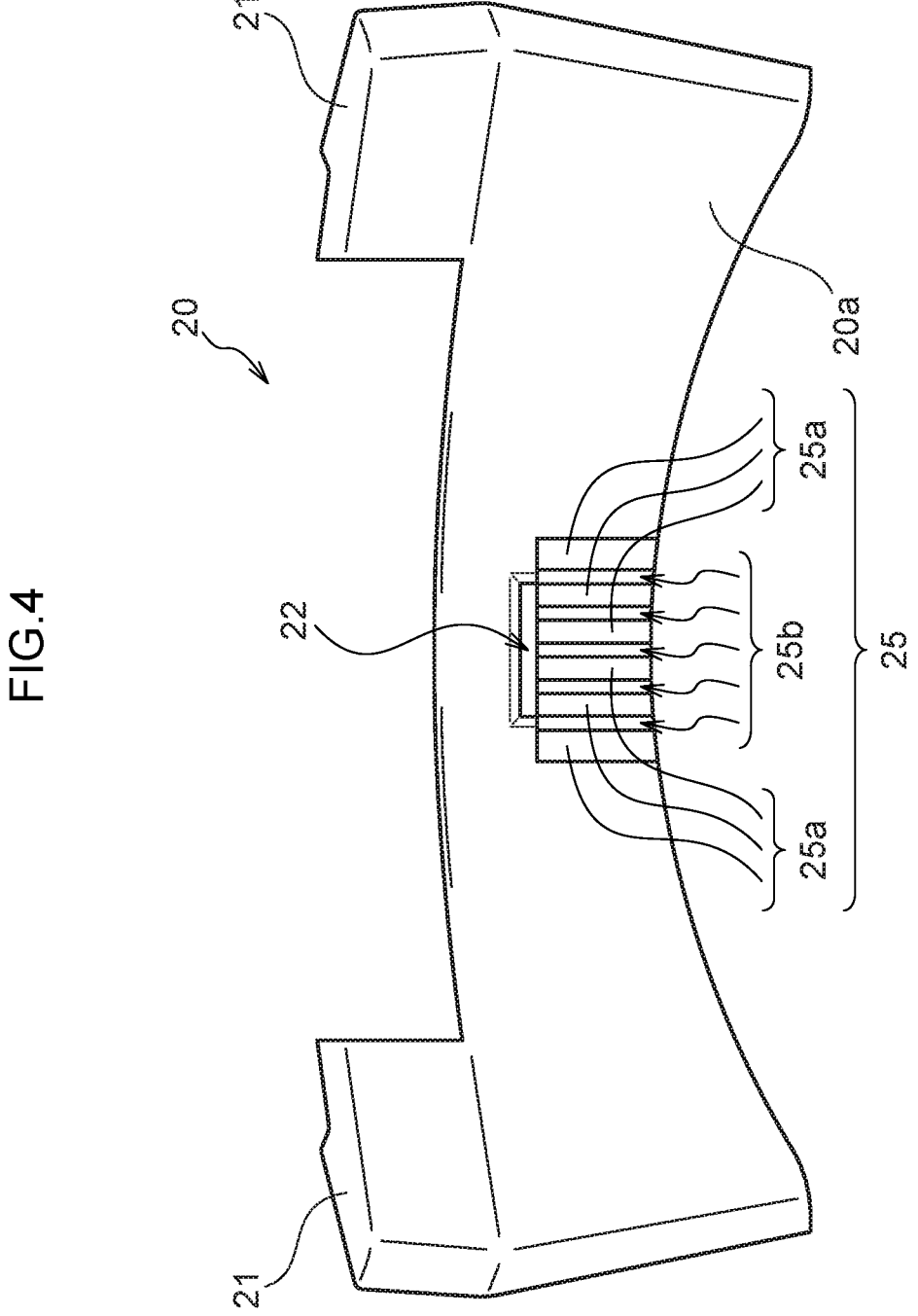
FIG. 4 is a front view of the protective cover.

Now, structures of the protective cover 20 are described. FIG. 3 is a front-upper perspective view of the protective cover 20, and FIG. 4 is a front view of the protective cover 20. As shown in FIG. 2, an end portion at the front face side of the measurement device 10 assumes a shape in which a central portion projects forward further than both left and right ends, and both the left and right ends are smoothly inflected toward the rear face side from the central portion. The protective cover 20 assumes a shape that is inflected toward the rear side to match the inflection of the front face side of the measurement device 10. In other words, for attachment of the protective cover 20 to the end portion of the measurement device 10 in which the insertion aperture 12 is provided, the protective cover 20 for the measurement device 10 is inflected such that the rear face side of the protective cover 20 is recessed to match the shape of the region of the end portion that includes the surroundings of the insertion aperture 12. Moreover, the protective cover 20 is provided with the opening portion 22, which enables insertion of the test strip 50. Greatly inflected portions at the rear face side of both the left and right ends of the protective cover 20 serve as side guards 21 that cover corner portions at both the left and right ends of the casing body 101. Means for attaching the protective cover 20 to the measurement device 10 is not limited; means for tightly fitting the side guards 21 and the corner portions at both the left and right ends of the casing body 101 to each other or the like may be provided. The opening portion 22, which is disposed at a central portion of a front face side 20a of the protective cover 20, penetrates between the front face side 20a and a rear face side 20b (see FIG. 5 and FIG. 6).

A plural number of front face side ribs 25a are formed from a front face side lower end edge of the opening portion 22. The front face side ribs 25a extend downward and protrude forward. In other words, upper end edges of the plural front face side ribs 25a are formed to be coplanar with and connected with the front face side lower edge of the opening portion 22. As shown in FIG. 3, interstices 25b are formed between the front face side ribs 25a in elongated slit shapes. The plural front face side ribs 25a and the plural interstices 25b formed between the adjacent front face side ribs 25a constitute a second drawing portion 25, into which a liquid sample is drawn by capillary force. As described later, the plural interstices 25b of the second drawing portion 25 that are between the plural ribs connecting to the front face side lower edge of the opening portion 22 act as capillaries. Thus, a surplus liquid sample arriving at the second drawing portion 25 may be drawn into the interstices 25b of the second drawing portion 25 by the capillary effect and accommodated there by surface tension. As shown in FIG. 3, the second drawing portion 25 projects in the front face direction relative to the opening portion 22. In the present disclosure, two, five, six or the like of the plural ribs and plural interstices of respective drawing portions are illustrated in the drawings but this does not limit the number thereof, which may be selected according to the width of the opening portion 22.

Figure 5:
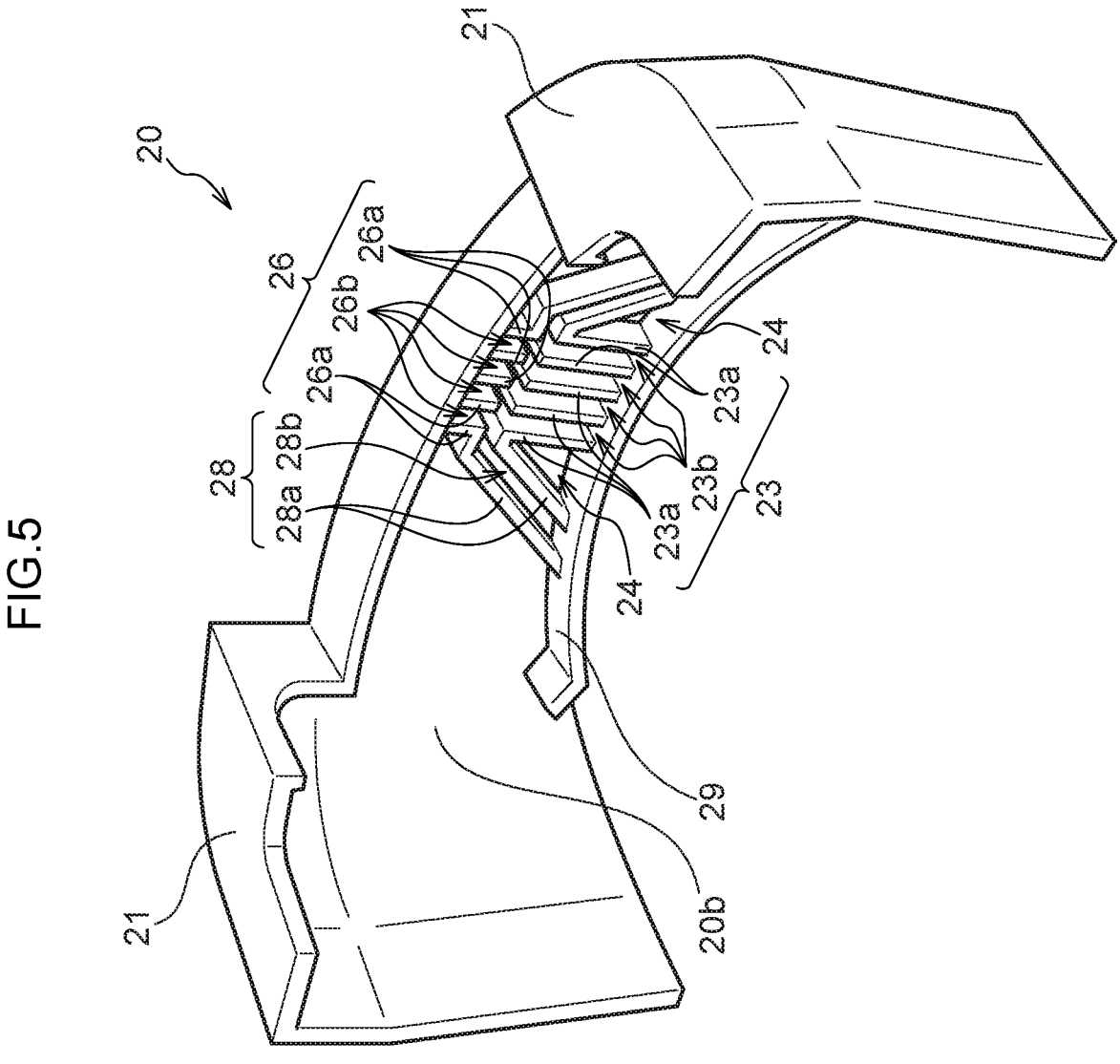
FIG. 5 is a rear-upper perspective view of the protective cover.
Figure 6:
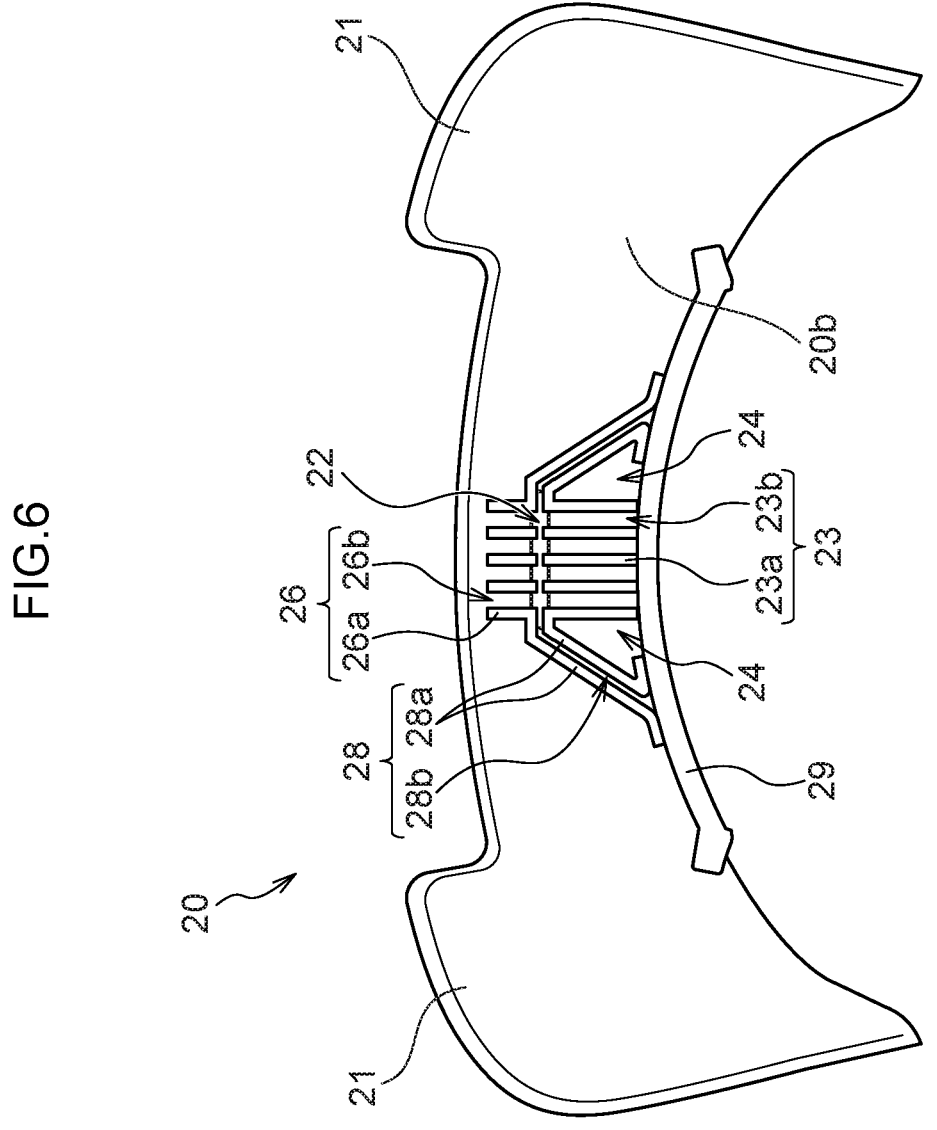
FIG. 6 is a rear view of the protective cover.

FIG. 5 is a rear-upper perspective view of the protective cover 20 and FIG. 6 is a rear view of the protective cover 20. As shown in FIG. 5 and FIG. 6, the rear face side 20b is inflected so to be recessed. The opening portion 22 is disposed at a central portion of the rear face side 20b of the protective cover 20. A plural number of rear face side ribs 23a are formed from a rear face side lower edge of the opening portion 22. The rear face side ribs 23a extend downward and protrude rearward. In other words, upper end edges of the plural rear face side ribs 23a are formed to be coplanar with and connected with the rear face side lower edge of the opening portion 22. Interstices 23b are formed between the rear face side ribs 23a in elongated slit shapes. The plural rear face side ribs 23a and the plural interstices 23b formed between the adjacent rear face side ribs 23a constitute a first drawing portion 23 into which a liquid sample is drawn by capillary force. As described later, the plural interstices 23b of the first drawing portion 23 that are between the plural ribs connecting to the rear face side lower edge of the opening portion 22 act as capillaries. A surplus liquid sample arriving at the first drawing portion 23 may be drawn into the interstices 23b of the first drawing portion 23 by the capillary effect and accommodated there by surface tension. As shown in FIG. 5, the first drawing portion 23 projects in the rear face direction relative to the opening portion 22. A flange 29 protrudes to the rear face side from a lower edge of the protective cover 20. Lower end edges of the rear face side ribs 23a are spaced apart from an upper face of the flange 29 and are not linked thereto.

A plural number of upward ribs 26a are formed from a rear face side upper edge of the opening portion 22. The upward ribs 26a extend upward and protrude rearward. In other words, lower end edges of the plural upward ribs 26a are formed to be coplanar with and connected with the rear face side upper edge of the opening portion 22. Interstices 26b are formed between the upward ribs 26a in long, narrow slit shapes. The plural upward ribs 26a and the plural interstices 26b formed between the upward ribs 26a constitute a third drawing portion 26 for drawing a liquid sample by capillary force. Moreover, inclined ribs 28a are formed from the lower ends of the upward ribs 26a that are disposed at both the left and right ends of the third drawing portion 26 and from the upper ends of the rear face side ribs 23*a* that are disposed at both the left and right ends of the first drawing portion 23. The inclined ribs 28*a* are angled downward toward the sides. Lower ends of the inclined ribs 28*a* are spaced apart from the upper face of the flange 29 and are not linked thereto.

As shown in the rear view of FIG. 6, both left and right ends of the opening portion 22 are surrounded by the corresponding pairs of the inclined ribs 28*a*. When a surplus liquid sample ingresses into the left and right end portions of the opening portion 22, the surplus liquid sample is drawn toward the flange 29 by slit-shaped interstices 28*b* that are formed between the pairs of inclined ribs 28*a*. Then, at each of the left and right ends of the opening portion 22, an inclined drawing portion 28 is formed by the pair of inclined ribs 28*a*, which extend at an angle downward to the side from the respective end portion of the opening portion 22, and the interstice 28*b* between the pair of inclined ribs 28*a*. At the rear face side, the opening portion 22 is surrounded by the first drawing portion 23, the third drawing portion 26 and the respective inclined drawing portions 28 at left and right. As described later, whatever position of the opening portion 22 a surplus liquid sample ingressing through the opening portion 22 ingresses from, that liquid sample is drawn and accommodated by one or more of the interstices 23*b*, the interstices 26*b* and the interstices 28*b*. The sample that cannot be accommodated in the interstices 23*b* and 28*b* may be drawn to the flange 29 and accumulated at the flange 29. The rear face side ribs 23*a* and inclined ribs 28*a* extend downward from the opening portion 22 towards the flange 29 but a distance is left open between the rear face side ribs 23*a* and inclined ribs 28*a* and the flange 29. Therefore, a space at the upper face of the flange 29 is not closed up and large amounts of the sample may be accumulated at the upper face of the flange 29 by surface tension. Furthermore, substantially triangular spaces are formed between the flange 29, the rear face side ribs 23*a* at both ends and the inclined ribs 28*a*, and these triangular spaces are linked with the space at the upper face of the flange 29. Thereby, even larger amounts of the sample may be accommodated. Therefore, the spaces at the upper face of the flange 29 including the substantially triangular spaces described above are referred to as liquid sumps 24 that accommodate a liquid sample that overflows from the first drawing portion 23.

Figure 7:
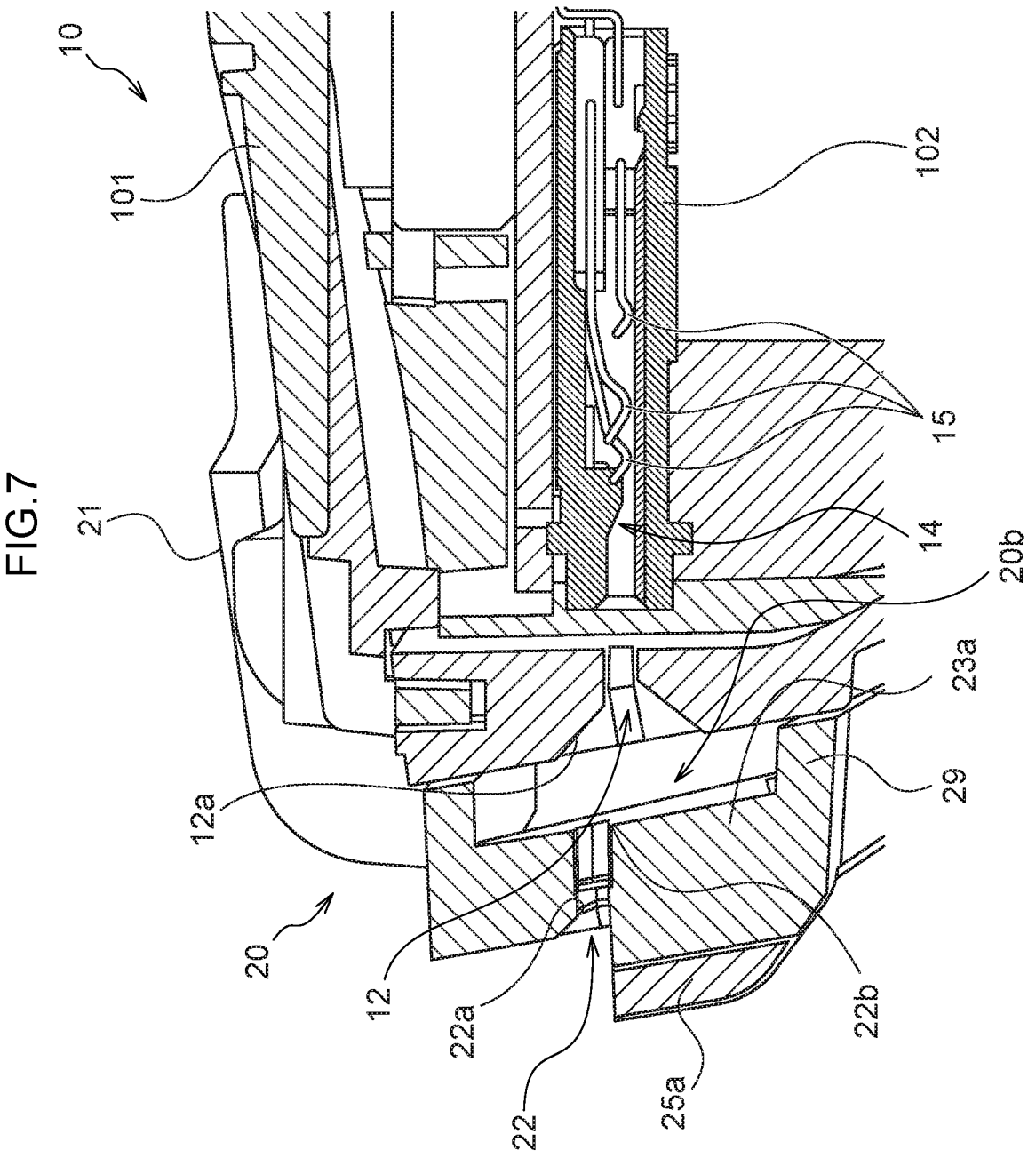
FIG. 7 is a section along VII-VII in FIG. 1, showing a magnification of a vicinity of an opening portion and an insertion aperture.

FIG. 7 is a section along VII-VII in FIG. 1. That is, FIG. 7 is a section cut along the center of the opening portion 22, showing a magnification of a vicinity of the opening portion 22 and the insertion aperture 12. As is shown in FIG. 7, in the state in which the protective cover 20 is attached to the casing body 101 enclosing the measuring instrument 102, the opening portion 22 is disposed at the upper side in the vertical direction relative to the insertion aperture 12. As shown in FIG. 7, the lower edge of the opening portion 22 is at the upper side relative to an upper edge of the insertion aperture 12 in the vertical direction. Moreover, beveling 12*a* is formed at edges of the insertion aperture 12. The beveling 12*a* smoothly links from the upper edge and lower edge of the insertion aperture 12 to an outer wall of the casing body 101. As shown in FIG. 7, the beveling 12*a* is formed as inclined surfaces. Moreover, an upper edge of the beveling 12*a* is disposed at the upper side relative to the lower edge of the opening portion 22. A portion of the beveling 12*a* is superposed in the front-rear direction with the lower edge of the opening portion 22. Furthermore, a deep interior space at the rear face side of the insertion aperture 12 serves as a test strip accommodation portion 14 in which the test strip 50

(see FIG. 8) is accommodated. Deeper inside, terminals 15 are provided that electronically connect with an electrode portion 52, which is described later.

Figure 8:
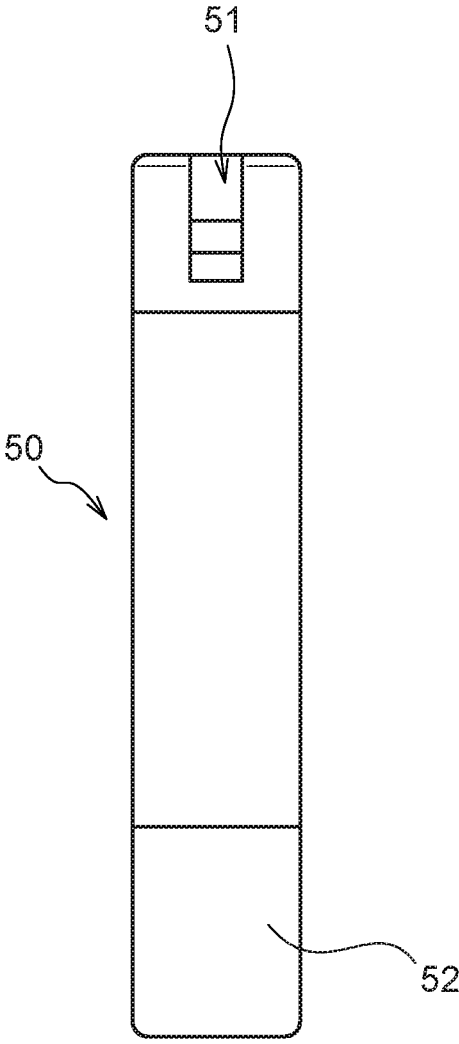
FIG. 8 is a plan view of a test strip.

In the present exemplary embodiment, the lower edge of the opening portion 22 is disposed at the upper side relative to the upper edge of the insertion aperture 12, but the upper edge of the insertion aperture 12 may be formed at the upper side relative to the lower edge of the opening portion 22. When the upper edge of the insertion aperture 12 is formed at the upper side relative to the lower edge of the opening portion 22, it is required that a height difference between the upper edge of the insertion aperture 12 and the lower edge of the opening portion 22 is specified to be smaller than a thickness of the test strip 50. Note that, in this case, if the thickness of the test strip 50 illustrated in FIG. 8 is represented by h, the difference between the upper edge of the insertion aperture 12 and the lower edge of the opening portion 22 is smaller than the thickness h. Thus, the test strip 50 is curved when inserted through the opening portion 22 into the insertion aperture 12.

As shown in FIG. 7, in the state in which the protective cover 20 is attached to the casing body 101, the rear face side ribs 23*a* and upward ribs 26*a* protruding rearward from the rear face side 20*b* of the protective cover 20, and specifically connecting to the edge portions of the opening portion 22, are spaced apart from the outer face of the casing body 101 that includes the insertion aperture 12, assuring a predetermined distance therebetween. Therefore, a liquid sample pooling in the ribs and spaces of the protective cover 20 is unlikely to come into contact with the measurement device 10.

FIG. 8 is a plan view schematically showing the test strip 50 that is employed at the measurement device 10 according to the present exemplary embodiment. Note that, in FIG. 8, the upper side is an upstream side and the lower side is a downstream side. The test strip 50 is formed of a material with flexibility. As shown in FIG. 8, the test strip 50 is in a sheet shape that is formed to be elongated. A slot-shaped spotting portion 51 into which a liquid sample is spotted is formed at the upstream side of the test strip 50. One end of an electrode that is used for measurement is exposed at the upstream side of the test strip 50. The electrode portion 52 is formed at another end of the electrode, which is exposed at the downstream side of the test strip 50. When the test strip 50 is attached to the measurement device 10, the electrode portion 52 makes contact with the terminals 15 provided at the measuring instrument 102 of the measurement device 10 (see FIG. 7). The test strip 50 has a structure in which an electrode fabricated of metal is sandwiched between two sheets of a material such as synthetic resin or the like that has flexibility.

For insertion of the test strip 50, the insertion aperture 12 and the opening portion 22 are formed in elongated slit shapes matching the shape of the test strip 50. As shown in FIG. 7, in the state in which the protective cover 20 is attached to the casing body 101, the opening portion 22 is at a higher position than the insertion aperture 12. In other words, the insertion aperture 12 and the opening portion 22 are offset in the vertical direction, and heights thereof from the bottom face of the measurement device 10 are different. Viewed from the front face of the measurement device 10, the upper edge of the opening portion 22 is disposed at the upper side, closer to the top face of the measurement device 10 than the upper edge of the insertion aperture 12. The lower edge of the opening portion 22 is also disposed at the upper side, closer to the top face of the measurement device 10 than the lower edge of the insertion aperture 12. Furthermore, the lower edge of the opening portion 22 is disposed at the upper side, closer to the top face of the measurement device 10 than the upper edge of the insertion aperture 12. In other words, in the vertical direction, the upper edge of the insertion aperture 12 is disposed at the lower side relative to the lower edge of the opening portion 22. Note that the upper edge of the insertion aperture 12 may be at the upper side relative to the lower edge of the opening portion 22, in which case it is sufficient that the difference between the upper edge of the insertion aperture 12 and the lower edge of the opening portion 22 is set to be smaller than the aforementioned thickness h of the test strip 50.

The measuring instrument 102 is accommodated inside the casing body 101 behind the insertion aperture 12. A space extending from the insertion aperture 12 serves as the test strip accommodation portion 14 in which the test strip 50 is accommodated (see FIG. 7). A path along which the test strip 50 proceeds from the insertion aperture 12 to the test strip accommodation portion 14 extends in the front-rear direction from the insertion aperture 12 to the test strip accommodation portion 14. The test strip 50 may proceed along the path in line with the path and may smoothly come into contact with the terminals 15 that are in the test strip accommodation portion 14 (see FIG. 7).

Figure 9:
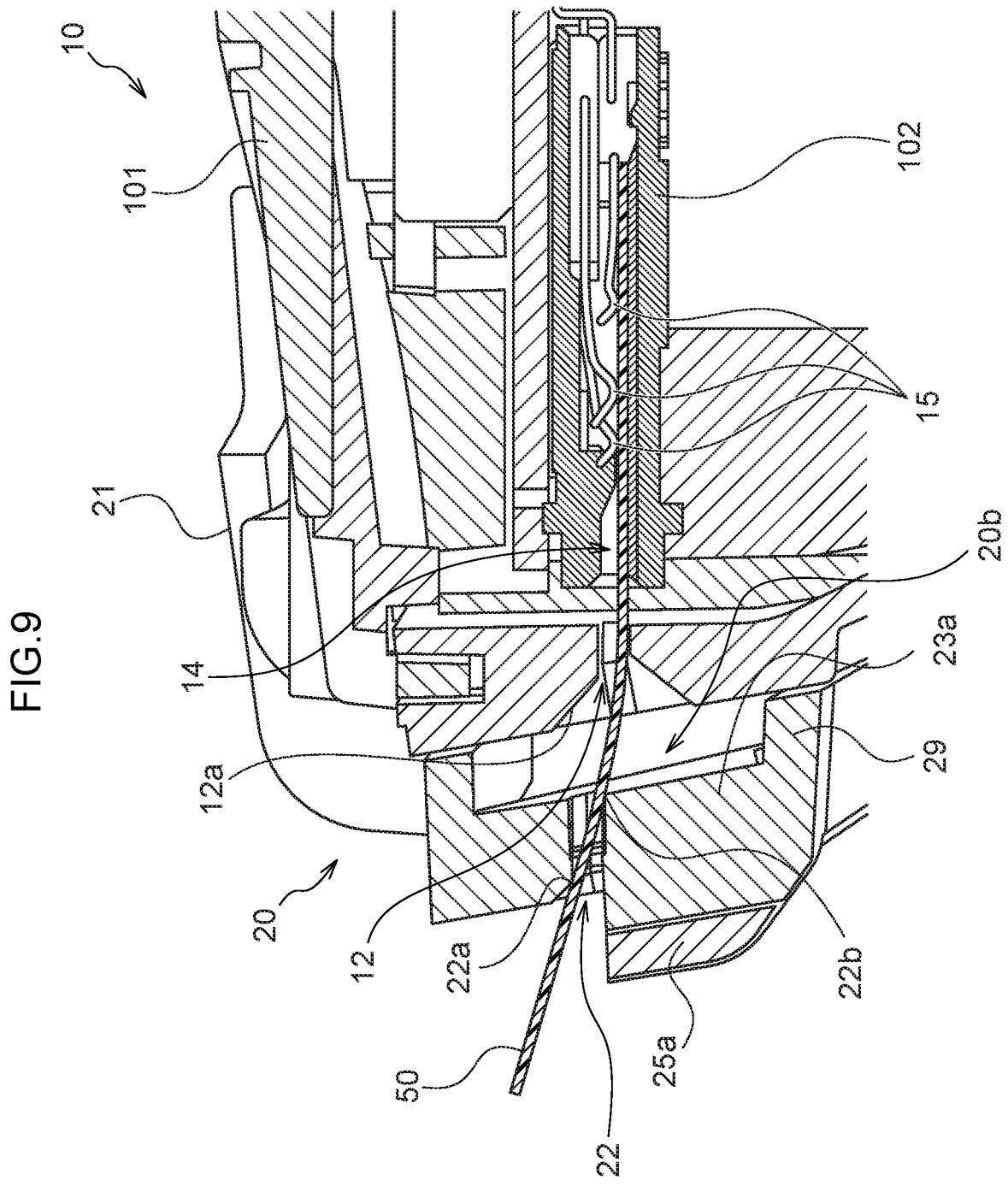
FIG. 9 is a sectional view showing a state in which the test strip is inserted into the measurement device shown in FIG. 7.

The sectional diagram of FIG. 9 shows a state in which the test strip 50 is inserted into the measurement device 10 shown in FIG. 7 in the state in which the protective cover 20 is attached to the casing body 101. Conditions while the test strip 50 is being inserted into the opening portion 22 of the protective cover 20 and the measurement device are described. Firstly, a distal end at the side of the test strip 50 at which the electrode portion 52 is disposed is placed on the second drawing portion 25 that protrudes forward. Because the upper end edge of the second drawing portion 25 is coplanar with the opening portion 22, the test strip 50 may be inserted along the second drawing portion 25 that protrudes forward and into the opening portion 22 that has a small width. Thereby, the test strip 50 may be inserted into the opening portion 22 more easily than if the second drawing portion 25 was absent.

Furthermore, when the test strip 50 is inserted along the second drawing portion 25 and into the opening portion 22, the distal end of the test strip 50 touches against the beveling 12*a* formed in the surroundings of the insertion aperture 12 of the casing body 101. As described above, the test strip 50 is formed in an elongated sheet shape and is flexible. Therefore, when the test strip 50 is inserted further, the distal end is smoothly guided with flexibility into the insertion aperture 12 that is disposed lower than the opening portion 22. Since a portion of the beveling 12*a* is superposed with the lower edge of the opening portion 22 in the front-rear direction, the distal end of the test strip 50 that has been placed on the lower edge of the opening portion 22 inevitably abuts against the beveling 12*a*. The beveling 12*a* is an inclined surface smoothly linking to the insertion aperture 12, and the test strip 50 may be easily inserted along the beveling 12*a* to the insertion aperture 12 that is disposed at the lower side relative to the opening portion 22.

As illustrated in FIG. 9, when the distal end of the test strip 50 that has proceeded horizontally from the second drawing portion 25 to the opening portion 22 is pushed further in the state in which the distal end is abutted against the beveling 12*a*, the distal end curves downward and is guided to the insertion aperture 12 that is at the lower side. When the distal end continues to be inserted further, the distal end of the test strip 50 passes through the insertion aperture 12, proceeds deeper into the test strip accommodation portion 14, and pushes the terminals 15 upward. When the test strip 50 reaches this state, the insertion of the test strip 50 is complete. In this state, the test strip 50 is slightly curved because of the height difference between the opening portion 22 and the insertion aperture 12. Therefore, the spotting portion 51 at the upstream side and the electrode portion 52 at the downstream side of the test strip 50 are at different heights in the vertical direction.

In this state, as shown in FIG. 9, a lower face of the test strip 50 that has been inserted into the insertion aperture 12 abuts against the upper end edges of the rear face side ribs 23*a* of the first drawing portion 23 (i.e., against a rear face side lower edge 22*b* of the opening portion 22), and an upper face of the test strip 50 abuts against a front face side upper edge 22*a* of the opening portion 22 of the protective cover 20. Because the flexible test strip 50 is curved, these abutting regions abut with area contact due to a force acting to restore the curvature. Note that, when the lower face of the test strip 50 abuts against the plural rear face side ribs 23*a*, gaps may be formed between the lower face of the test strip 50 and the interstices 23*b* between the rear face side ribs 23*a*.

Moreover, the opening portion 22 is formed such that the left-right direction width of the opening portion 22 is a little longer than the width of the test strip 50. Thereby, in the state in which the test strip 50 is inserted into the measurement device 10 to which the protective cover 20 is attached, small gaps are formed between the respective left and right edges of the opening portion 22 and left and right edges of the test strip 50. Furthermore, the plural rear face side ribs 23*a* that form the first drawing portion 23 are disposed orthogonally to the lower face side of the test strip 50 that has been inserted into the insertion aperture 12. Based on the structure described above, the following occurs when a surplus blood sample has been spotted onto the test strip 50. Note that the meaning of the term "surplus blood sample" as used in the present exemplary embodiment is intended to include a blood sample with a portion exceeding an amount required for measurement.

As described above, the upper face of the test strip 50 abuts against the front face side upper edge 22*a* of the opening portion 22. Thereby, even if a surplus blood sample spotted onto the spotting portion 51 of the test strip 50 flows along the upper face of the test strip 50, ingression of some amount of the blood sample to the inside of the protective cover 20 is blocked by this abutting region (below referred to as a "first abutting portion"). Moreover, depending on the amount of the surplus blood sample, the surplus blood sample may simply remain at this first abutting portion due to surface tension. Note that a likelihood of the surplus blood sample flowing to this first abutting portion is essentially very low, and, in many cases, the blood sample would flow down to the lower face of the test strip 50 due to gravity.

When a surplus blood sample flows along the lower face of the test strip 50 and reaches the gaps formed between the lower face of the test strip 50 and the interstices 23*b*, the surplus blood sample may be drawn into the interstices 23*b* by capillary force. Depending on the amount of the surplus blood sample, the surplus blood sample may simply be accommodated in the interstices 23*b*. However, when the surplus blood sample is large, the surplus blood sample flows to the flange 29 and is accumulated at the flange 29 by surface tension. Moreover, when a surplus blood sample flows along the upper face or lower face of the test strip 50, the surplus blood sample may flow sideways to both sides of the test strip 50. The blood sample flowing along both sides of the test strip 50 passes through the gaps between the left and right walls of the opening portion 22 and the test strip 50, and may be drawn into the inclined drawing portions 28. Noted that, since the first drawing portion 23 and the inclined drawing portions 28 are spaced apart from the flange 29 at the lower side, even if a portion of the surplus blood sample cannot be accommodated in the first drawing portion 23 and the inclined drawing portions 28, the portion may be accumulated in the aforementioned liquid sumps 24.

Figure 10:
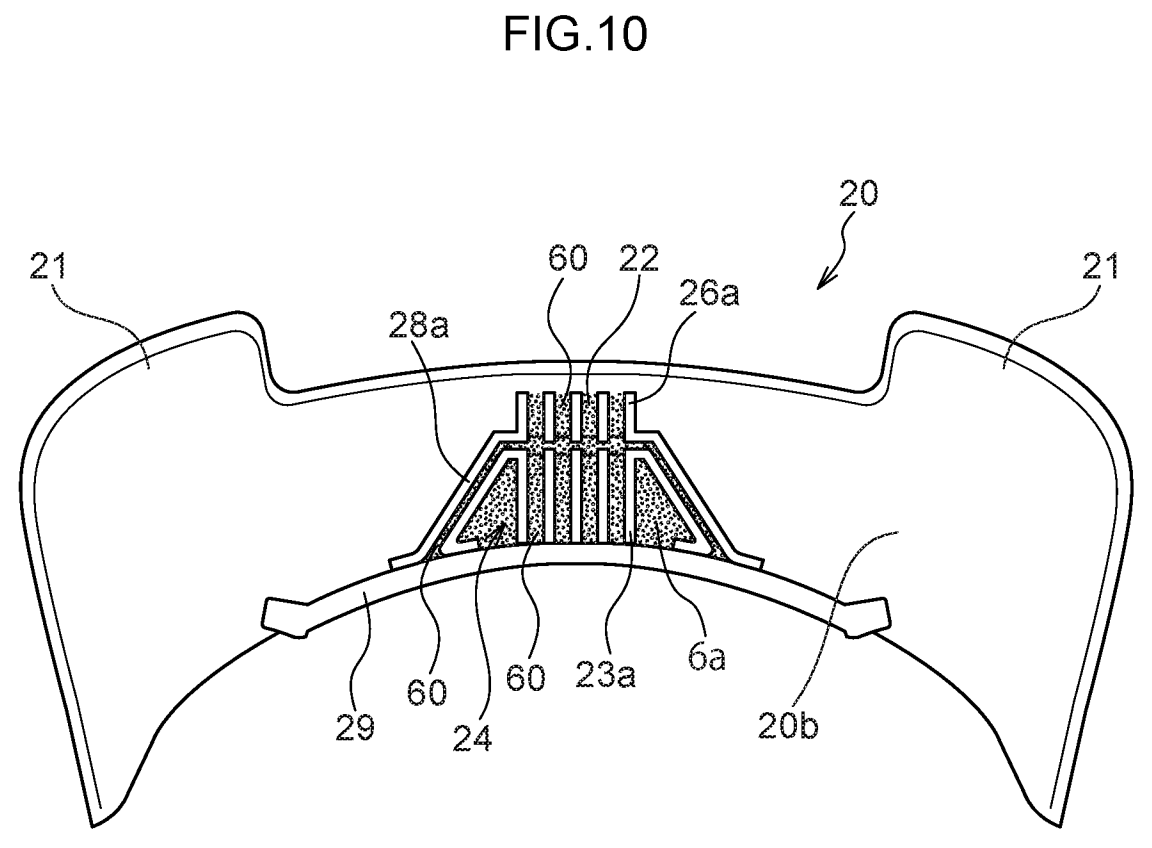

In other words, when a surplus blood sample 60 ingresses to the rear face side of the protective cover 20, as illustrated in the rear view of FIG. 10, depending on an amount of the surplus blood sample 60, the surplus blood sample 60 is captured by the first drawing portion 23, the third drawing portion 26 and the inclined drawing portions 28. Moreover, a portion that cannot be absorbed by the first drawing portion 23, the third drawing portion 26 and the inclined drawing portions 28 is captured at the liquid sumps 24. Further, since the rear face side 20b of the protective cover 20 and the first drawing portion 23 are spaced apart from the insertion aperture 12 of the measurement device 10 and the outer face of the casing body 101 (see FIG. 9), the surplus blood sample 60 that is captured by the first drawing portion 23, the third drawing portion 26 and the liquid sumps 24 does not reach the insertion aperture 12 and the casing body 101.

Figure 11:
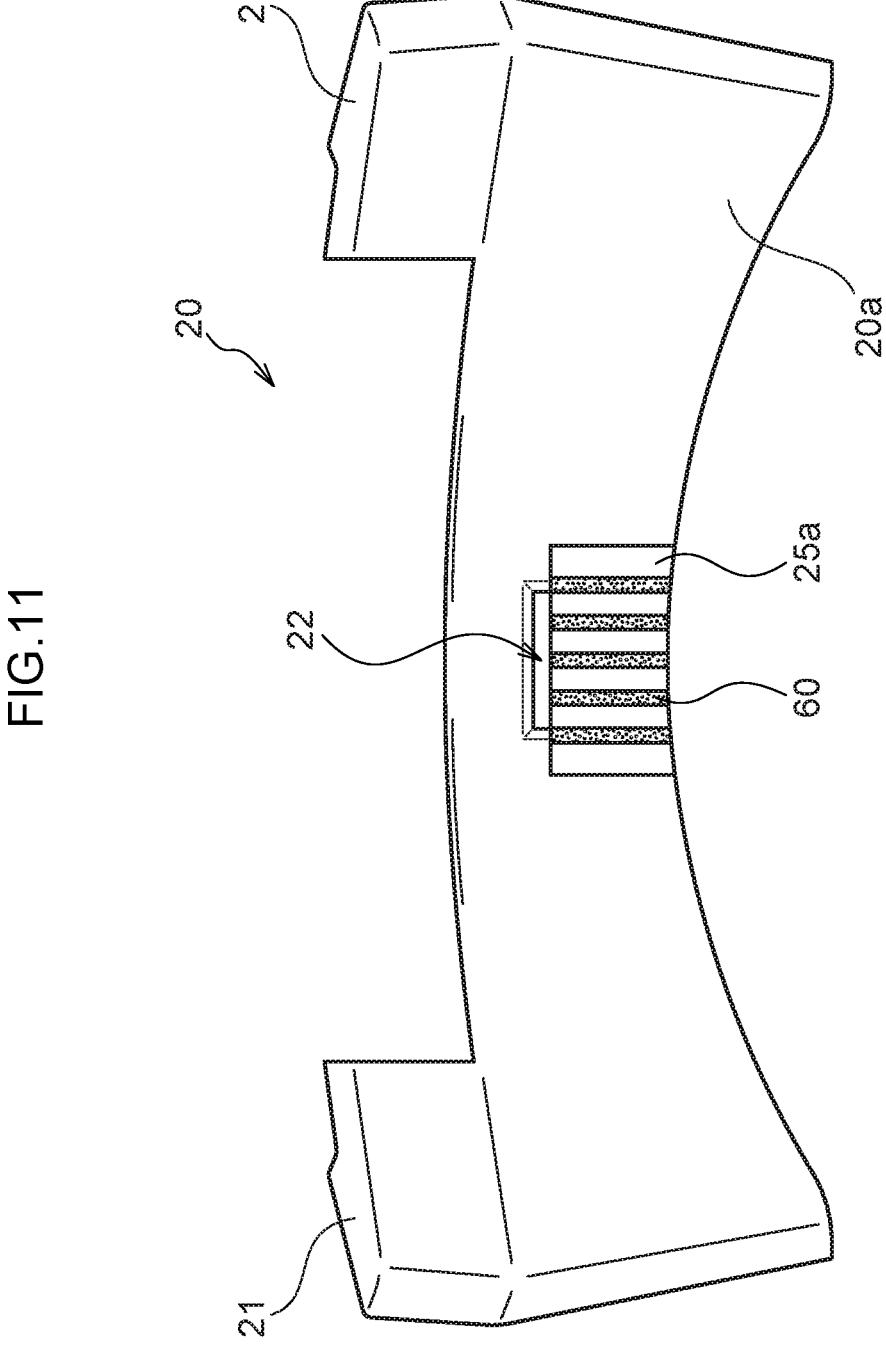
FIG. 11 schematically shows flows of the surplus blood sample at a front face side of the protective cover.

Note that, as illustrated in the front view of FIG. 11, some amount of the surplus blood sample 60 may be also captured at the front face side of the protective cover 20, at the second drawing portion 25.

Moreover, the first drawing portion 23, the second drawing portion 25, the third drawing portion 26 and the inclined drawing portions 28 are not only be structured by ribs and interstices between the ribs, but also be structured by attaching a fibrous material capable of absorbing a sample in the liquid state at the corresponding position.

As illustrated in the exemplary embodiment described above, the protective cover 20 is attached to be removable from the measurement device 10 of the present disclosure. Thereby, when the protective cover 20 is soiled by a sample, the protective cover 20 may be replaced with a new protective cover 20, or the protective cover 20 may be cleaned and then reattached.

In the exemplary embodiment described above, in the state in which the protective cover 20 is attached to the casing body 101, the insertion aperture 12 and the opening portion 22 are offset in the vertical direction and heights thereof from the bottom face of the measurement device 10 are different. In this structure, flexibility of the test strip 50 is utilized to insert the test strip 50 through the opening portion 22 to the insertion aperture 12 with a different height. As in the exemplary embodiment described above, it is preferable that the opening portion 22 is at a higher position than the insertion aperture 12. However, the opening portion 22 may be formed so as to be at a lower position than the insertion aperture 12.

INDUSTRIAL APPLICABILITY

The present invention is applicable to a measurement device for measuring a sample of blood, urine or the like in a liquid state, such as a blood sugar measurement device.

What is claimed is:

1. A measurement device to which a protective cover is attached, wherein:

the measurement device comprises an insertion aperture for insertion of a test strip onto which a liquid sample is spotted;

the protective cover is attached to the measurement device so as to cover a region including surroundings of the insertion aperture, and the protective cover includes an opening portion into which the test strip is insertable;

the opening portion and the insertion aperture are relatively positioned such that, in a state in which the test strip is inserted through the opening portion and inserted into the insertion aperture, an upper face and a lower face of the test strip both abut against the protective cover, the insertion aperture and the opening portion are offset in a vertical direction, and a first drawing portion is provided at a rear face side lower edge of the opening portion, the first drawing portion drawing the liquid sample by capillary force.

2. The measurement device according to claim 1, wherein edges of the insertion aperture are beveled.

3. The measurement device according to claim 1, wherein the first drawing portion includes a plurality of ribs that are connected to the rear face side lower edge of the opening portion, and includes interstices between adjacent ribs.

4. The measurement device according to claim 3, wherein the plurality of ribs are orthogonal to a lower face side of the test strip in the state in which the test strip is inserted into the insertion aperture.

5. The measurement device according to claim 1, wherein a rear face side of the protective cover is spaced apart from the insertion aperture.

6. The measurement device according to claim 1, wherein a liquid sump is formed at a rear face side of the protective cover, the liquid sump accommodating the liquid sample that overflows from the first drawing portion.

7. The measurement device according to claim 1, wherein a second drawing portion is provided at a front face side lower edge of the opening portion, the second drawing portion drawing the liquid sample by capillary force.

8. The measurement device according to claim 7, wherein the second drawing portion includes a plurality of ribs that are connected to the front face side lower edge of the opening portion, and includes interstices between adjacent ribs.

9. The measurement device according to claim 1, wherein inclined drawing portions are provided at both left and right ends of the rear face side of the opening portion, the inclined drawing portions drawing the liquid sample by capillary force.

* * * * *